(12) United States Patent
Markert et al.

(10) Patent No.: US 8,580,775 B2
(45) Date of Patent: Nov. 12, 2013

(54) USE OF DERIVATIVES OF SINAPINIC ACID AND COMPOSITIONS COMPRISING SUCH DERIVATIVES

(75) Inventors: Thomas Markert, Monheiml (DE); Philippe Moussou, Tomblaine (FR); Louis Danoux, Saulxures les Nancy (FR); Andreas Rathjens, Tomblaine (FR)

(73) Assignee: Cognis IP Management GmbH, Duesseldorf (DE)

(*) Notice: Subject to any disclaimer, the term of this patent is extended or adjusted under 35 U.S.C. 154(b) by 216 days.

(21) Appl. No.: 12/530,037

(22) PCT Filed: Feb. 26, 2008

(86) PCT No.: PCT/EP2008/001492
§ 371 (c)(1),
(2), (4) Date: Sep. 4, 2009

(87) PCT Pub. No.: WO2008/107093
PCT Pub. Date: Sep. 12, 2008

(65) Prior Publication Data
US 2010/0130605 A1    May 27, 2010

(30) Foreign Application Priority Data
Mar. 6, 2007   (EP) .................................. EP07004523

(51) Int. Cl.
*A61K 31/33*   (2006.01)
*A01N 43/00*   (2006.01)

(52) U.S. Cl.
USPC ............. 514/183; 514/546; 514/543; 560/61; 560/254

(58) Field of Classification Search
USPC ..................... 514/543, 546; 560/61, 254, 546
See application file for complete search history.

(56) References Cited

U.S. PATENT DOCUMENTS

2004/0247536 A1   12/2004   Chaudhuri

FOREIGN PATENT DOCUMENTS

| EP | 0 450 892 A1 | 9/1991 |
|---|---|---|
| EP | 0 848 947 A1 | 6/1998 |
| EP | 1 437 117 A1 | 7/2004 |
| EP | 1 591 099 A2 | 11/2005 |
| JP | 64-013017 | 1/1989 |
| JP | 04-009355 | 1/1992 |
| JP | 09-165353 | 6/1997 |
| JP | 10-175838 | 6/1998 |
| JP | 2004-175778 | 6/2004 |
| JP | 2005503365 | 2/2005 |
| JP | 2005503430 | 2/2005 |
| WO | WO 99/59986 A1 | 11/1999 |
| WO | WO-03/007906 | 1/2003 |
| WO | WO 03/027055 A1 | 4/2003 |
| WO | WO 2006/124985 A1 | 11/2006 |
| WO | WO-2006/124989 | 11/2006 |

OTHER PUBLICATIONS

JP1013017 A, English Abstract.*
http://www.mhhe.com/physsci/chemistry/carey/student/olc/graphics/carey04oc/ref/ch20reactionsamides.html#hydrolysis. Published on Apr. 19, 2002 as evidenced by wayback machine.*
Sedivy et al "Aging by epigenetics—a consequence of chromatin damage?" experimental cell research, 2008, vol. 314, pp. 1909-1917.*
Lamberts et al "The endocrinology of aging", Science, vol. 278, Oct. 17, 1997, pp. 419-424.*
Patani et al "Bioisosterism: A Rational Approach in Drug Design", Chem., Rev., 1996, 96 (8), 3147-3176.*
Machine translation of JP11080091 A, 1999.*

* cited by examiner

*Primary Examiner* — Brandon Fetterolf
*Assistant Examiner* — Jean Cornet
(74) *Attorney, Agent, or Firm* — Servilla Whitney LLC

(57) ABSTRACT

The present invention relates to substances which can be used as cosmetic ingredients, especially for skin whitening and as cosmetic agents against signs of ageing skin. The present invention also relates to the use of such substances for the manufacture of a medicament for the treatment of disorders related to the pigmentation of the skin. The invention furthermore relates to specific substances.

6 Claims, No Drawings

USE OF DERIVATIVES OF SINAPINIC ACID AND COMPOSITIONS COMPRISING SUCH DERIVATIVES

CROSS REFERENCE TO RELATED APPLICATIONS

This application is the National Phase entry of PCT/EP2008/001492, filed Feb. 26, 2008 which claims priority to EPO patent application number 07004523 filed Mar. 6, 2007 both of which are incorporated herein by reference in their entireties.

FIELD OF THE INVENTION

The present invention relates to substances which can be used as cosmetic ingredients, especially for skin whitening and as cosmetic agents against signs of ageing skin. The present invention also relates to the use of such substances for the manufacture of a medicament for the treatment of disorders related to the pigmentation of the skin. The invention furthermore relates to specific substances.

There is a global market demand for whitening agents in cosmetics to prevent and/or decrease abnormal pigmentations, such as freckles or spots. These are pigmentations due to over exposure to sun. Additionally some dark-skinned individuals prefer lighter skin colour which is regarded as a particular beauty feature.

BACKGROUND OF THE INVENTION

EP 1 437 117 A1 (Cognis France) discloses sinapic acid (=3,5,-dimethoxy-4-hydroxycinnamic acid, =(3,5-dimethoxy-4-hydroxy-phenly)-3-prop-2-enoic acid, =sinapinic acid) and its derivatives as cosmetic ingredients. The derivatives are referenced in claim 15 and in paragraph [0025]: the derivatives obtained according to this paragraph are all derivatives via the acid function of sinapic acid. Derivatives via the 4-Hydroxygroup of the phenyl group or via the alkylene group adjacent to the acid group are not disclosed. EP 1 437 117 also cites the problem of instability for sinapic acid and proposes as solution a microencapsulation.

JP 64-013017 (Pola Chemical Industries) discloses derivatives of 3,5-dimethoxy-4-hydroxycinnamic acid. All the derivatives disclosed are derivatives via the acid function of the sinapic acid. No derivatives of the 4-hydroxygroup or the alkylene group are described.

JP 2004175778 A (Sogo Pharmaceutical Co) discloses cinnamic acid derivatives as cosmetic ingredient. All derivatives disclosed carry a specific group (2) or (3) on the acid moiety of the cinnamic acid. These substances are not encompassed by the substances according to the present invention.

WO 03/027055 A (Pacific Corporation) discloses thymyl or carvacryl esters of 3,4,5-trimethoxy phenyl acetate, 3,4,5-trimethoxy cinnamate or 3,4,5-trimethoxyhydrocinnamate and their use as whitening compositions.

Aim of the invention was to provide substances which can be effectively used for the manufacture of or in cosmetic compositions and which are especially suitable as skin whitener and/or as cosmetic agents against the signs of skin ageing. Of special interest was to provide substances which are chemically stable and can thus be easily incorporated into cosmetic compositions. In addition it is desired that these substances do not, or only to a much lower extent than products known in the market, cause an irritation of the skin onto which it is applied. A further aim of the invention was to provide substances for the manufacture of a medicament for the treatment of disorders related to the pigmentation of the skin. The invention furthermore relates to specific substances.

DETAILED DESCRIPTION OF PREFERRED EMBODIMENTS

The present invention relates to the use of at least one substance of formula (I)

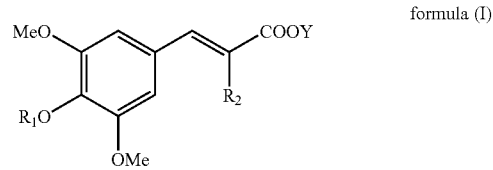

formula (I)

wherein
Y is H, C1-C8 alkyl, C2-C8 alkenyl, phenyl, $Na^+$, $K^+$ or $NH_4^+$,
$R_1$ and $R_2$ are independently from each other H, a linear or branched, saturated or unsaturated alkyl group comprising 1 to 18 carbon atoms or —C(=O)—$R_3$, wherein $R_3$ is a linear or branched, saturated or unsaturated alkyl group comprising 1 to 17 carbon atoms, and
wherein if $R_1$ is H or $CH_3$, then $R_2$ is not H,
for the manufacture of or in cosmetic and/or topical compositions for the lightening and/or whitening of skin and/or for the reduction of pigmentation and/or reduction of hyperpigmentation and/or inhibition of melanogenesis and/or for the prevention and/or retardation of signs of ageing and/or improving the skin appearance of aged skin.

Substances According to Formula (I)

Suitable according to the invention are substances according to formula (I)

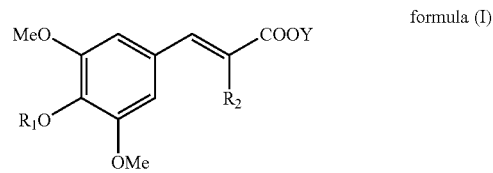

formula (I)

wherein
Y is H, C1-C8 alkyl, C2-C8 alkenyl, phenyl, $Na^+$, $K^+$ or $NH_4^+$,
$R_1$ and $R_2$ are independently from each other H, a linear or branched, saturated or unsaturated alkyl group comprising 1 to 18 carbon atoms or —C(=O)—$R_3$, wherein $R_3$ is a linear or branched, saturated or unsaturated alkyl group comprising 1 to 17 carbon atoms, and
wherein if $R_1$ is H or $CH_3$, then $R_2$ is not H.

The term "unsaturated alkyl group" encompasses any hydrocarbon moiety which comprises at least one double or at least one triple bond. Thus "unsaturated alkyl group" is used to encompass any alkenyl or alkenyl group.

Substituent Y

Y is selected from the group consisting of H, an alkyl or alkenyl group comprising 1 to 8 carbon atoms, a phenyl group, $Na^+$, $K^+$ or $NH_4^+$. In a preferred embodiment Y is selected from the group consisting of H, C1-C8 alkyl and C2-C8 alkenyl. The alkyl or alkenyl groups can be linear or branched. Examples of alkyl or alkenyl groups comprising 1 to 8 carbon atoms are Methyl, Ethyl, Propyl-, iso-Propyl [=1-Methylethyl-], Propenyl-, Isobutyl [2-Methylpropyl], sec-Butyl [=1-Methylpropyl], tert-Butyl [1,1-Dimethylethyl], But-2-enyl, But-3-enyl, But-1-enyl, n-Pentyl, 1-Methylbutyl-, 2-Methylbutyl-, 3-Methylbutyl, 1-Ethylpropyl-, 1,1-Dimethylpropyl, 1,2-Dimethylpropyl, 2,2-Dimethylpropyl, 1-Pentenyl-, 2-Pentenyl-, 3-Pentenyl-, 4-Pentenyl, Hexyl-, 1-Methylpentyl-, 2-Methylpentyl, 3-Methylpentyl, 4-Methylpentyl, 1-Ethylbutyl-, 2-Ethylbutyl-, 3-Ethylbutyl-, 1-Hexenyl, 2-Hexenyl, 3-Hexenyl, 4-Hexenyl-, 5-Hexenyl, Heptyl, 1-Methylhexyl-, 2-Methylhexyl-, 3-Methylhexyl-, 4-Methylhexyl-, 5-Methylhexyl, 1-Hepentyl, 2-Heptenyl, 3-Heptenyl-, 4-Heptenyl-, 5-Heptenyl, 6-Heptenyl-, n-Octyl, 2-Ethylhexyl-,1,1,3,3-Tetramethylbutyl.

In a preferred embodiment Y is selected from the group consisting of H, C1-C3 alkyl, C2-C3 alkenyl, $Na^+$ and $K^+$. In an especially preferred embodiment of the invention Y is H.

Substituent $R_1$ and $R_2$ $R_1$ and $R_2$ are independently from each other H, a linear or branched, saturated or unsaturated alkyl group comprising 1 to 18 carbon atoms or —C(=O)—$R_3$, wherein $R_3$ is a linear or branched, saturated or unsaturated alkyl group comprising 1 to 17 carbon atoms, provided that when if $R_1$ is H or $CH_3$, then $R_2$ is not H.

In a preferred embodiment $R_1$ and $R_2$ are independently of each other H, a linear or branched, saturated or unsaturated alkyl group comprising 1 to 12 carbon atoms, preferably 2 to 10 carbon atoms, or —C(=O)—$R_3$, wherein $R_3$ is a linear or branched, saturated or unsaturated alkyl comprising 1 to 11 carbon atoms, preferably 2 to 9 carbon atoms, provided that when $R_1$ is H or $CH_3$, then $R_2$ is not H.

In one embodiment $R_1$ and $R_2$ are —C(=O)—$R_3$, wherein $R_3$ is a linear or branched, saturated or unsaturated alkyl group comprising 1 to 17 carbon atoms.

In a preferred embodiment $R_1$ and $R_2$ are —C(=O)—$CH_3$.

In a preferred embodiment $R_2$ is C(=O)—$C_2H_5$ and $R_1$ is —C(=O)—$CH_3$

In a preferred embodiment $R_1$ is C(=O)—$C_2H_5$ and $R_2$ is —C(=O)—$CH_3$

Examples of suitable alkyl or alkenyl groups comprising 1 to 18 carbon atoms are Methyl, Ethyl, Propyl-, iso-Propyl [=1-Methylethyl-], Propenyl-, Isobutyl [2-Methylpropyl], sec-Butyl [=1-Methylpropyl], tert-Butyl [1,1-Dimethylethyl], But-2-enyl, But-3-enyl, But-1-enyl, n-Pentyl, 1-Methylbutyl-, 2-Methylbutyl-, 3-Methylbutyl, 1-Ethylpropyl-, 1,1-Dimethylpropyl, 1,2-Dimethylpropyl, 2,2-Dimethylpropyl, 1-Pentenyl-, 2-Pentenyl-, 3-Pentenyl-, 4-Pentenyl, Hexyl-, 1-Methylpentyl-, 2-Methylpentyl, 3-Methylpentyl, 4-Methylpentyl, 1-Ethylbutyl-, 2-Ethylbutyl-, 3-Ethylbutyl-, 1-Hexenyl, 2-Hexenyl, 3-Hexenyl, 4-Hexenyl-, 5-Hexenyl, Heptyl, 1-Methylhexyl-, 2-Methylhexyl-, 3-Methylhexyl-, 4-Methylhexyl-, 5-Methylhexyl, 1-Hepentyl, 2-Heptenyl, 3-Heptenyl-, 4-Heptenyl-, 5-Heptenyl, 6-Heptenyl-, n-Octyl, 2-Ethylhexyl-,1,1,3,3-Tetramethylbutyl, Nonyl-, Decyl-, Dodecyl-, Tridecyl-, Tetradecyl-, Pentadecyl-, Hexadecyl-, Heptadecyl-, Octadecyl-.

In a preferred embodiment $R_1$ and $R_2$ are independently of each other —C(=O)—$R_3$, wherein $R_3$ is a linear or branched, saturated or unsaturated alkyl group comprising 1 to 17 carbon atoms and at least $R_1$ or $R_2$ is H. In this embodiment either $R_1$ is H and $R_2$ is —C(=O)—$R_3$, wherein $R_3$ is a linear or branched, saturated or unsaturated alkyl group comprising 1 to 17 carbon atoms or $R_1$ is —C(=O)—$R_3$, wherein $R_3$ is a linear or branched, saturated or unsaturated alkyl group comprising 1 to 17 carbon atoms and $R_2$ is H, the latter alternative being preferred.

In a preferred embodiment $R_1$ is —C(=O)—$CH_3$ or —C(=O)—$C_2H_5$ and $R_2$ is H.

In a preferred embodiment $R_1$ is H, $R_2$ is C(=O)—$CH_3$ and Y is $CH_2$—$CH_3$.

In a preferred embodiment $R_1$ is —C(C=O)—$CH_3$, $R_2$ is H and Y is H.

The following table exemplifies substances according to formula (I) to be used according to the invention:

TABLE 1

| Substance | Y= | $R_1$= | $R_2$= |
|---|---|---|---|
| 1a | —H | —H | —CH3 |
| 1b | —H | —H | —C2H5 |
| 1c | —H | —H | —C(=O)—CH3 |
| 1d | —H | —H | —C(=O)—C2H5 |
| 2a | —H | —CH3 | —C2H5 |
| 2b | —H | —CH3 | —CH3 |
| 2c | —H | —CH3 | —C(=O)—CH3 |
| 2d | —H | —CH3 | —C(=O)—C2H5 |
| 3a | —H | —C2H5 | —H |
| 3b | —H | —C2H5 | —CH3 |
| 3c | —H | —C2H5 | —C2H5 |
| 3d | —H | —C2H5 | —C(=O)—CH3 |
| 3e | —H | —C2H5 | —C(=O)—C2H5 |
| 4a | —H | —C(=O)—CH3 | —H |
| 4b | —H | —C(=O)—CH3 | —CH3 |
| 4c | —H | —C(=O)—CH3 | —C2H5 |
| 4d | —H | —C(=O)—CH3 | —C(=O)—CH3 |
| 4e | —H | —C(=O)—CH3 | —C(=O)—C2H5 |
| 5a | —H | —C(=O)—C2H5 | —H |
| 5b | —H | —C(=O)—C2H5 | —CH3 |
| 5c | —H | —C(=O)—C2H5 | —C2H5 |
| 5d | —H | —C(=O)—C2H5 | —C(=O)—CH3 |
| 5e | —H | —C(=O)—C2H5 | —C(=O)—C2H5 |
| 6a | —CH3 | —H | —CH3 |
| 6b | —CH3 | —H | —C2H5 |
| 6c | —CH3 | —H | —C(=O)—CH3 |
| 6d | —CH3 | —H | —C(=O)—C2H5 |
| 7a | —CH3 | —CH3 | —C2H5 |
| 7b | —CH3 | —CH3 | —CH3 |
| 7c | —CH3 | —CH3 | —C2H5 |
| 7d | —CH3 | —CH3 | —C(=O)—CH3 |
| 7e | —CH3 | —CH3 | —C(=O)—C2H5 |
| 8a | —CH3 | —C2H5 | —H |
| 8b | —CH3 | —C2H5 | —CH3 |
| 8c | —CH3 | —C2H5 | —C2H5 |
| 8d | —CH3 | —C2H5 | —C(=O)—CH3 |
| 8e | —CH3 | —C2H5 | —C(=O)—C2H5 |
| 9a | —CH3 | —C(=O)—CH3 | —H |
| 9b | —CH3 | —C(=O)—CH3 | —CH3 |
| 9c | —CH3 | —C(=O)—CH3 | —C2H5 |
| 9d | —CH3 | —C(=O)—CH3 | —C(=O)—CH3 |
| 9e | —CH3 | —C(=O)—CH3 | —C(=O)—C2H5 |
| 10a | —CH3 | —C(=O)—C2H5 | —H |
| 10b | —CH3 | —C(=O)—C2H5 | —CH3 |
| 10c | —CH3 | —C(=O)—C2H5 | —C2H5 |
| 10d | —CH3 | —C(=O)—C2H5 | —C(=O)—CH3 |
| 10e | —CH3 | —C(=O)—C2H5 | —C(=O)—C2H5 |
| 11a | —C2H5 | —H | —CH3 |
| 11b | —C2H5 | —H | —C2H5 |
| 11c | —C2H5 | —H | —C(=O)—CH3 |
| 11d | —C2H5 | —H | —C(=O)—C2H5 |
| 12a | —C2H5 | —CH3 | —C2H5 |
| 12b | —C2H5 | —CH3 | —CH3 |
| 12c | —C2H5 | —CH3 | —C2H5 |
| 12d | —C2H5 | —CH3 | —C(=O)—CH3 |
| 12e | —C2H5 | —CH3 | —C(=O)—C2H5 |
| 13a | —C2H5 | —C2H5 | —H |
| 13b | —C2H5 | —C2H5 | —CH3 |
| 13c | —C2H5 | —C2H5 | —C2H5 |
| 13d | —C2H5 | —C2H5 | —C(=O)—CH3 |
| 13e | —C2H5 | —C2H5 | —C(=O)—C2H5 |
| 14a | —C2H5 | —C(=O)—CH3 | —H |
| 14b | —C2H5 | —C(=O)—CH3 | —CH3 |
| 14c | —C2H5 | —C(=O)—CH3 | —C2H5 |
| 14d | —C2H5 | —C(=O)—CH3 | —C(=O)—CH3 |
| 14e | —C2H5 | —C(=O)—CH3 | —C(=O)—C2H5 |
| 15a | —C2H5 | —C(=O)—C2H5 | —H |

TABLE 1-continued

| Substance | Y= | R₁= | R₂= |
|---|---|---|---|
| 15b | —C2H5 | —C(=O)—C2H5 | —CH3 |
| 15c | —C2H5 | —C(=O)—C2H5 | —C2H5 |
| 15d | —C2H5 | —C(=O)—C2H5 | —C(=O)—CH3 |
| 15e | —C2H5 | —C(=O)—C2H5 | —C(=O)—C2H5 |
| 16a | —C3H7(*) | —H | —CH3 |
| 16b | —C3H7 | —H | —C2H5 |
| 16c | —C3H7 | —H | —C(=O)—CH3 |
| 16d | —C3H7 | —H | —C(=O)—C2H5 |
| 17a | —C3H7 | —CH3 | —C2H5 |
| 17b | —C3H7 | —CH3 | —CH3 |
| 17c | —C3H7 | —CH3 | —C2H5 |
| 17d | —C3H7 | —CH3 | —C(=O)—CH3 |
| 17e | —C3H7 | —CH3 | —C(=O)—C2H5 |
| 18a | —C3H7 | —C2H5 | —H |
| 18b | —C3H7 | —C2H5 | —CH3 |
| 18c | —C3H7 | —C2H5 | —C2H5 |
| 18d | —C3H7 | —C2H5 | —C(=O)—CH3 |
| 18e | —C3H7 | —C2H5 | —C(=O)—C2H5 |
| 19a | —C3H7 | —C(=O)—CH3 | —H |
| 19b | —C3H7 | —C(=O)—CH3 | —CH3 |
| 19c | —C3H7 | —C(=O)—CH3 | —C2H5 |
| 19d | —C3H7 | —C(=O)—CH3 | —C(=O)—CH3 |
| 19e | —C3H7 | —C(=O)—CH3 | —C(=O)—C2H5 |
| 20a | —C3H7 | —C(=O)—C2H5 | —H |
| 20b | —C3H7 | —C(=O)—C2H5 | —CH3 |
| 20c | —C3H7 | —C(=O)—C2H5 | —C2H5 |
| 20d | —C3H7 | —C(=O)—C2H5 | —C(=O)—CH3 |
| 20e | —C3H7 | —C(=O)—C2H5 | —C(=O)—C2H5 |

(*) the substituent "—C3H7" in this table can be either Propyl or iso-Propyl [1-Methylethyl]

Cosmetic Compositions

Cosmetic compositions shall mean any preparation intended to be placed in contact with the various external parts of the human body (epidermis, hair system, nails, lips and external genital organs) or with the teeth and the mucous membranes of the oral cavity with a view exclusively or mainly to cleaning them, perfuming them, changing their appearance and/or correcting body odours and/or protecting them or keeping them in good condition.

The cosmetic compositions according to the invention can for example be in the form of hair shampoos, hair lotions, foam baths, shower baths, creams, gels, lotions, alcoholic and aqueous/alcoholic solutions, emulsions, wax/fat masses, stick preparations, powders or ointments. These compositions can also comprise, as further auxiliaries and additives, mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, anti-dandruff agents, film formers, swelling agents, insect repellents, self-tanning agents, hydrotropes, solubilizers, preservatives, perfume oils, dyes and the like.

The substance according to formula (I) can be used in cosmetic and/or topical compositions in an amount of 0.0001 to 10 weight-% based on the total weight of the composition, preferably in an amount of 0.001 to 5, especially in an amount of 0.01 to 3 weight-% based on the total weight of the composition.

The present invention also relates to cosmetic and/or topical compositions comprising a substance according to formula (I) and at least one skin-whitening active.

The invention encompasses the finding that substances of formula (I) are advantageously to be used as skin-whitening active. It is to be understood that compositions according to claim 2 of the present invention comprise at least one substance according to formula (I) [preferably as a skin-whitener] and at least one (other) skin-whitening active, which is different from a substance according to formula (I). In this preferred embodiment the two actives can act synergistically to provide a highly efficient cosmetic composition.

Skin-Whitening Actives

The further skin-whitening active can be chosen from any known skin-whitening agent, e.g. kojic acid, hydroquinone, alpha- and beta-arbutin, other hydroquinone glycosides, deoxyarbutin, ferulic acid, diacetyl-boldine, azelaic acid, octadecenedioic acid, linoleic acid, conjugated linoleic acid, alpha-lipoic acid, glutathione and derivatives, undecylenoyl-phenylalanine, vitamin C and derivatives as magnesium L-ascorbyl-phosphate, niacinamide, 4-n-butyl-resorcinol, alpha- and beta-hydroxy acids, ellagic acid, resveratrol, *Morus alba* extracts, glabridin and liquorice extracts, imperatorin and isoimperatorin and *Angelica dahurica* extracts, centaureidin and Yarrow extracts, *Bellis perennis* extracts, *Phyllanthus emblica* extracts, water cress extracts, *Veratum nigrum* extracts, *Sophora flavescens* extracts, ascomycete-derived melanin-degrading enzyme.

In one embodiment of the invention the further skin-whitening active is at least one plant extract.

In one embodiment of the invention the further skin-whitening active is selected from the group consisting of kojic acid, alpha- and beta-arbutin, other hydroquinone glycosides, deoxyarbutin, ferulic acid, conjugated linoleic acid, vitamin C and derivatives as magnesium L-ascorbyl-phosphate, niacinamide and/or liquorice extracts.

The substances of formula (I) to be used according to the invention as well as the compositions according to claim 6 are suitably used for the lightening and/or whitening of skin and/or for the reduction of pigmentation and/or reduction of hyperpigmentation and/or inhibition of melanogenesis.

The invention encompasses the finding that substances of formula (I) as well as the compositions according to claim 6 are suitably used for the prevention and/or retardation of signs of ageing and/or improving the skin appearance of aged skin.

The invention is further directed to the use of a substance according to formula (I) for the manufacture of a medicament for the treatment of a disease connected to a disorder in the pigmentation of the skin.

Such hyperpigmentation diseases are for example chloasma (a hypersecretion of melanin induced by hormonal factors and amplified by the effects of sun exposure), lentigines, solar and senile lentigo, Dubreuilh melanosis, melasma, or any form of hypermelanosis or melanocyte dysfunction.

Some of the substances according to formula (I) are novel substances. Thus a further embodiment of the invention is directed to these novel substances.

Substances According to Formula (II)

The invention is directed to substances of formula (II).

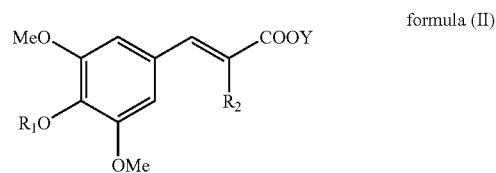

formula (II)

wherein

Y is of H, C1-C8 alkyl, C2-C8 alkenyl, phenyl, Na⁺, K⁺ or NH₄⁺,

R₁ and R₂ are independently from each other H, a linear or branched, saturated or unsaturated alkyl group comprising 1 to 18 carbon atoms, or —C(=O)—R₃, wherein R₃ is a linear or branched, saturated or unsaturated alkyl group comprising 1 to 17 carbon atoms, and wherein if $R_1$ is H and $R_2$ is $CH_3$, then Y is an alkyl group comprising 3 to 8 carbon atoms, a phenyl group, $Na^+$, $K^+$ or $NH_4^+$, wherein if $R_1$ is $COCH_3$, and $R_2$ is H, Y is a linear or branched, saturated or unsaturated alkyl group comprising 3 to 8 carbon atoms, a phenyl group, $Na^+$, $K^+$ or $NH_4^+$, wherein if $R_1$ is $CH_3$, and $R_2$ is $CH_3$ Y is a linear or branched, saturated or unsaturated alkyl group comprising 3 to 8 carbon atoms, a phenyl group, $Na^+$, $K^+$ or $NH_4^+$, wherein if $R_1$ is $CH_3$, and $R_2$ $COCH_3$, Y is a linear or branched, saturated or unsaturated alkyl group comprising 4 to 8 carbon atoms, a phenyl group, $Na^+$, $K^+$ or $NH_4^+$ wherein if $R_1$ is $CH_3$ and $R_2$ is —$CH_2$—CH=$CH_2$, Y is a linear or branched, saturated or unsaturated alkyl group comprising 3 to 8 carbon atoms, a phenyl group, $Na^+$, $K^+$ or $NH_4^+$ wherein if $R_1$ is H and $R_2$ is $COCH_3$ Y is an alkyl group comprising 1 carbon atom, a phenyl group, $Na^+$, $K^+$ or $NH_4^+$, wherein if Y is H and $R_2$ is $CH_3$, $R_1$ is not a linear C14 alkyl moiety.

wherein if $R_1$ is $CH_3$ and $R_2$ is H, Y is not H or a phenyl group

Examples for substances according to formula (II) are listed in table 1 as substances 1b, 1d, 2a, 2d, 3a, 3b, 3c, 3d, 3e, 4b, 4c, 4d, 4e, 5a, 5b, 5c, 5d, 5e, 6b, 6c, 6d, 7a, 7c, 7e, 8a, 8b, 8c, 8d, 8e, 9b, 9c, 9d, 9e, 10a, 10b, 10c, 10d, 10e, 11b, 11d, 12a, 12c, 12e, 13a, 13b, 13c, 13d, 13e, 14b, 14c, 14d, 14e, 15a, 15b, 15c, 15d, 15e, 16a, 16b, 16d, 17°, 17b, 17c, 17e, 18a, 18b, 18c, 18d, 18e, 19a, 19b, 19c, 19d, 19e, 20a, 20b, 20c, 20d, 20e.

Additional substances according to formula (II) are listed in table 2.

TABLE 2

Further examples of substances according to formula (II)

| Substance | Y= | $R_1$= | $R_2$= |
|---|---|---|---|
| 16e | —C4H9 (n-Butyl) | —H | —CH3 |
| 16f | —C4H9(1-Methyl-propyl) | —H | —CH3 |
| 16g | -n-Pentyl | —H | —CH3 |
| 16h | -n-Hexyl | —H | —CH3 |
| 16g | -n-Octyl | —H | —CH3 |
| 17f | —C4H9 (n-Butyl) | —CH3 | —CH3 |
| 17g | —C4H9(1-Methyl-propyl) | —CH3 | —CH3 |
| 17h | -n-Pentyl | —CH3 | —CH3 |
| 17i | -n-Hexyl | —CH3 | —CH3 |
| 17j | -n-Octyl | —CH3 | —CH3 |
| 17k | —C4H9 (n-Butyl) | —CH3 | —C(=O)—CH3 |
| 17l | —C4H9(1-Methyl-propyl) | —CH3 | —C(=O)—CH3 |
| 17m | -n-Pentyl | —CH3 | —C(=O)—CH3 |
| 17n | -n-Hexyl | —CH3 | —C(=O)—CH3 |
| 17o | -n-Octyl | —CH3 | —C(=O)—CH3 |
| 19f | —C4H9 (n-Butyl) | —C(=O)—CH3 | —H |
| 19g | —C4H9(1-Methyl-propyl) | —C(=O)—CH3 | —H |
| 19h | -n-Pentyl | —C(=O)—CH3 | —H |
| 19i | -n-Hexyl | —C(=O)—CH3 | —H |
| 19j | -n-Octyl | —C(=O)—CH3 | —H |

A preferred embodiment of the invention is directed to substances according to formula (III)

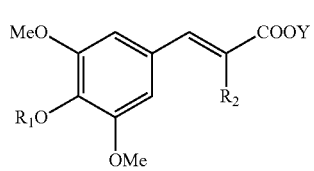

formula (III)

Y is H, C1-C8 alkyl, C2-C8 alkenyl, phenyl, $Na^+$, $K^+$ or $NH_4^+$, $R_1$ and $R_2$ are independently from each other H, a linear or branched, saturated or unsaturated alkyl group comprising 1 to 18 carbon atoms, or —C(=O)—$R_3$, wherein $R_3$ is a linear or branched, saturated or unsaturated alkyl group comprising 1 to 17 carbon atoms, and wherein if $R_1$ is H then $R_2$ is not H, —$CH_3$ or $COCH_3$ wherein if $R_1$ is $CH_3$, then $R_2$ is not $CH_3$, —$CH_2$—CH=$CH_2$ or $COCH_3$ wherein if $R_1$ is $COCH_3$, $R_2$ is not H wherein if Y is H and R2 is CH3, R1 is not a linear C14 alkyl moiety.

wherein if $R_1$ is $CH_3$ and $R_2$ is H, Y is not H or a phenyl group

Examples for substances according to formula (III) are listed in table 1 as substances 1b, 1d, 2a, 2d, 3a, 3b, 3c, 3d, 3e, 4b, 4c, 4d, 4e, 5a, 5b, 5c, 5d, 5e, 6b, 6d, 7a, 7c, 7e, 8a, 8b, 8c, 8d, 8e, 9b, 9c, 9d, 9e, 10a, 10b, 10c, 10d, 10e, 11b, 11d, 12a, 12c, 12e, 13a, 13b, 13c, 13d, 13e, 14b, 14c, 14d, 14e, 15a, 15b, 15c, 15d, 15e, 16b, 16d, 17a, 17c, 17e, 18a, 18b, 18c, 18d, 18e, 19b, 19c, 19d, 19e, 20a, 20b, 20c, 20d, 20e.

Substances according to formula (II) and (III) are encompassed by substances according to formula (I). Thus the use and compositions as claimed for substances according to formula (I) are also valid for the substances according to formula (II) and (III).

EXAMPLES

Example 1

Synthesis of acetoxysinapic acid (Substance 4a of Table 1)

Synonym: 3,5-dimethoxy-4-acetoxy-cinnamic acid
Chemical Abstracts Number: 113158-15-9

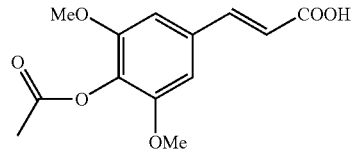 [SMILES: COc1cc(/C=C/C(=O)O)cc(OC)c1OC(C)=O]

Batch: 1) 2 kg (11 moles) syringaldehyde; 2) 8.64 kg acetic anhydride; 3) 0.01 kg 4-N,N-dimethylaminopyridine, 4) 0.902 kg sodium acetate, 5) 3.349 kg acetic anhydride Procedure: 1) syringaldehyde, 2) acetic anhydride and 3) 4-N,N-dimethylaminopyridine were stirred together in a 50 liters vessel at room temperature for 3 hours. A rise in temperature indicated the exothermic reaction. The mixture was stirred over night at 20° C. and acetic acid and excess acetic anhydride were removed by distillation at 0.8 mbar. After 3 hours, distillation was complete and the vacuum was replaced with nitrogen. 4) sodium acetate was added and 5) fresh acetic anhydride was added and the mixture was heated under vigorous stirring to reflux temperatures of 140° C. for 17 hours. After cooling down to 80° C., 8 kg water were added to the reaction mixture and the mixture was again heated to 140° C. and then cooled to 0° C. The crystallised product was filtered and washed with cold water yielding 3.650 kg of a wet residue. 30 liters filtrate was again filled into the reaction vessel and chilled again but no precipitation occurred in this case. The reaction product was dried under vacuum to give 2.3 kg raw acetylsinapinic acid (yield 85%). The 2.3 kg raw material was suspended in 24.4 kg ethanol and 8 kg water and the mixture was refluxed at 74° C. while 40 g active charcoal was added. After some minutes reflux the mixture was filtered at 70° C. to remove the charcoal. The filtrates and washes (altogether 37.1 kg) were put back into the reaction vessel and 19.9 kg solvent was removed under vacuum. 17.1 kg crystallised product in solvent were filtrated to yield 2.360 kg pure acetylsinapinic acid which left 1.660 kg material after drying (61.4% yield, melting point 195-202° C.).

Example 2

Synthesis of sinapylacetoacetate (Substance 11c of Table 11)

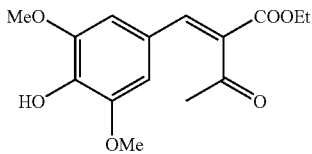 [SMILES: CCOC(=O)/C(=C/c1cc(OC)c(O)c(OC)c1)C(C)=O]

Chemical Abstracts Number: 491851-34-4

50.1 g (0.28 mol) syringaldehyde and 61.2 g (0.47 mol) ethyl acetoacetate were placed in a vessel and 100 ml ethanol and 2 ml piperidine was added. The mixture was heated at reflux temperatures for about 2 hours. On cooling to room temperature yellow crystals appear which were filtrated and re-crystallized from ethanol, yield was 21.2 g.

Example 3

Melanogenesis Inhibition Assay

Melanocytes (B16 cell line) were inoculated in standard medium of cell culture with foetal calf serum (FCS). After an incubation of 3 days at 37° C. under 5% $CO_2$, growth medium was exchanged for standard medium with a range of concentrations for each compound to be tested and a control without ingredient. After an incubation of 3 days, the level of melanin was measured by recording the optical density at 475 nm. After washing the cells with a balanced salt buffer, and homogenisation in a solution of 0.1 M NaOH, the number of viable cells was determined by evaluation of the level of cellular proteins (Bradford's method).

The results are expressed in % against control (cell culture medium without compound) as a mean+/−SEM (Standard Error of Mean) on 2 or 3 assays, each in triplicate.

TABLE 3

Rate of cellular proteins & melanin in %/control (mean +/− SEM on 3 assays in triplicate):

| | Dose % (w/v) | Protein level | Melanin level |
|---|---|---|---|
| Control | — | 100 +/− 0 | 100 +/− 0 |
| Compound according example 1 | 0.0003 | 100 +/− 1 | 86 +/− 2 |
| | 0.001 | 95 +/− 1 | 67 +/− 2 |
| | 0.003 | 93 +/− 3 | 26 +/− 1 |
| | 0.01 | 81 +/− 10 | 19 +/− 2 |
| Compound according example 2 | 0.001 | 110 +/− 10 | 108 +/− 3 |
| | 0.003 | 123 +/− 9 | 54 +/− 6 |

The results demonstrated that the compounds according to example 1 and 2 have decreased the rate of melanin synthesis in melanocytes, without cell toxicity.

What is claimed is:

1. A method of preparing a cosmetic and/or topical composition, the method comprising: providing a substance of formula (I)

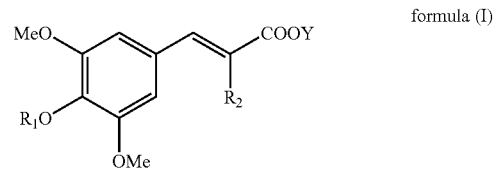

wherein
Y is H;
$R_1$ is —C(=O)—$CH_3$; and
$R_2$ is H,
the method comprising adding the substance of formula (I) to a cosmetic and/or topical base,
wherein said composition is effective for the lightening and/or whitening of skin, and/or reduction of pigmentation, and/or reduction of hyperpigmentation, and/or inhibition of melanogenesis, and/or retardation of signs of ageing, and/or improving the appearance of aged skin.

2. The method of claim 1, wherein the substance of formula (I) is present in an amount of 0.0001 to 10 weight-% based on the total weight of the composition.

3. The method of claim 2, wherein the substance of formula (I) is present in an amount of 0.01 to 3 weight-% based on the total weight of the composition.

4. The method of claim 1, further comprising adding at least one further skin-whitening active.

5. The method of claim 1, further comprising at least one auxiliary and/or additive.

6. The method of claim 1, wherein the cosmetic and/or topical composition is selected from the group consisting of hair shampoos, hair lotions, foam baths, shower baths, creas, gels, lotions, alcoholic and aqueous/alcoholic solutions, emulsions, was/fat masses, stick preparations, powders and ointments.

* * * * *